US 6,660,533 B2

(12) United States Patent
Mallet et al.

(10) Patent No.: US 6,660,533 B2
(45) Date of Patent: *Dec. 9, 2003

(54) ATTACHING A BIOLOGICAL MOLECULE TO A SUPPORT SURFACE

(75) Inventors: François Mallet, Villeurbanne (FR); Alain Theretz, Ecully (FR); Eric Perouzel, Paris (FR); Christine Hebrard, Irigny (FR)

(73) Assignee: Bio Merieux, Marcy L'Etoile (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/647,983

(22) PCT Filed: Apr. 12, 1999

(86) PCT No.: PCT/FR99/00848
§ 371 (c)(1),
(2), (4) Date: Oct. 6, 2000

(87) PCT Pub. No.: WO99/53321
PCT Pub. Date: Oct. 21, 1999

(65) Prior Publication Data
US 2003/0082658 A1 May 1, 2003

(30) Foreign Application Priority Data
Apr. 10, 1998 (FR) .............................. 98 04879

(51) Int. Cl.$^7$ ............................................ G01N 33/543
(52) U.S. Cl. .................... 436/518; 436/524; 436/501; 435/7.1; 435/7.92
(58) Field of Search .................... 436/518, 524, 436/525, 527, 532, 823, 501; 435/6, 7.1, 69.1, 7.92, 69.7; 427/528

(56) References Cited

U.S. PATENT DOCUMENTS

| 5,492,814 | A | | 2/1996 | Weissleder |
| 5,627,079 | A | * | 5/1997 | Gardella et al. ............ 436/525 |
| 6,020,026 | A | * | 2/2000 | Birch et al. ................. 427/287 |
| 6,207,391 | B1 | * | 3/2001 | Wu et al. .................... 435/7.1 |

FOREIGN PATENT DOCUMENTS

| EP | 0 368 208 A | 5/1990 |
| EP | 0 482 571 A | 4/1992 |
| EP | 0 272 792 A | 6/1998 |
| EP | 0 874 242 A | 10/1998 |
| FR | 2 758 884 | 7/1998 |
| FR | 2 762 394 | 10/1998 |
| FR | 2 764 988 | 12/1998 |
| WO | WO 91 02980 | 3/1991 |

* cited by examiner

Primary Examiner—Long V. Le
Assistant Examiner—Gary W. Counts
(74) Attorney, Agent, or Firm—Oliff & Berridge, PLC

(57) ABSTRACT

The invention concerns a method for fixing a biological molecule, associated with a specific binding site, on the surface of a support made of silica or metal oxide. The invention also concerns a surface functionalized by the method and the use of such a surface. The method is characterized in that it consists in: functionalizing the surface by cleaning, using at least a solvent or an oxygen plasma or any other process for forming alcohol groups on the support surface, to make it hydrophilic; contacting the biological molecule on said functionalized surface; and functionalizing the support by fixing the biological molecule specific binding site on at least one of the support alcohol groups. The invention is particularly useful in the field of biomedical diagnosis.

13 Claims, 2 Drawing Sheets

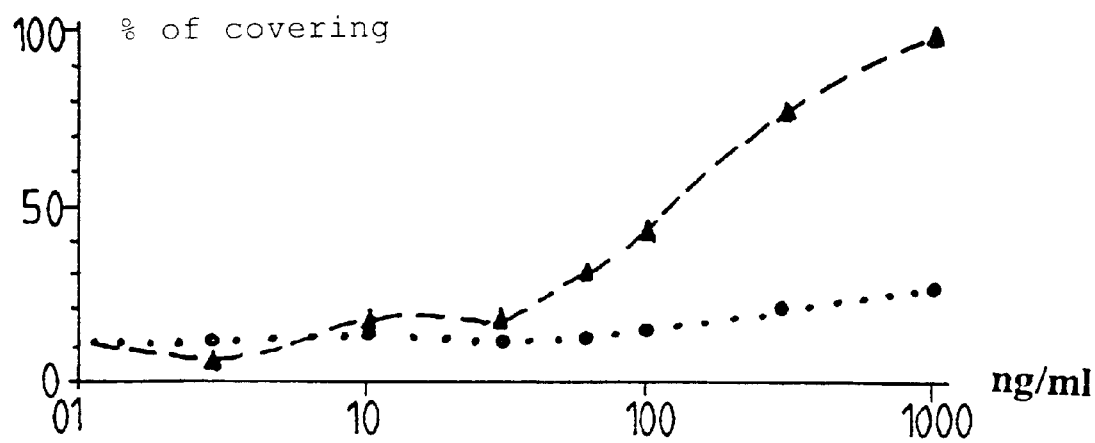
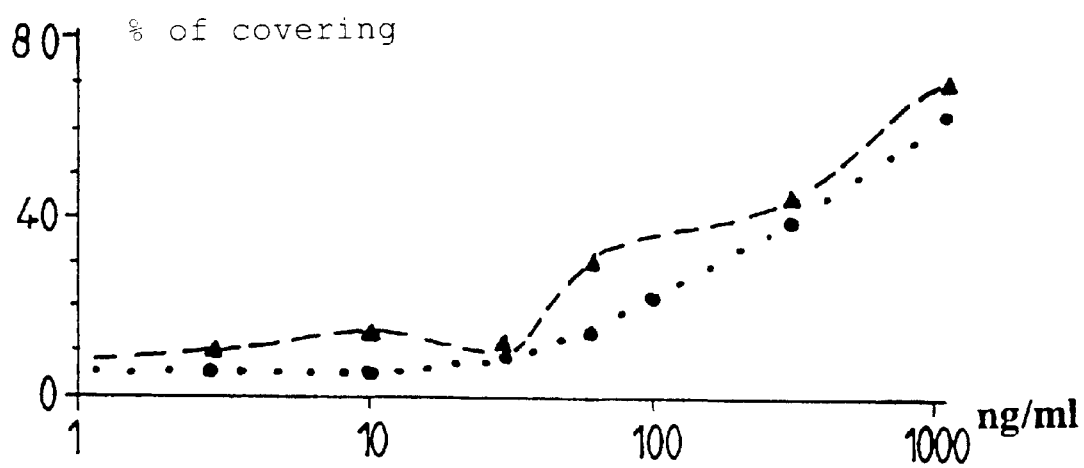

ATTACHING A BIOLOGICAL MOLECULE TO A SUPPORT SURFACE

BACKGROUND

1. Field of the Invention

The present invention relates to a method for attaching a biological molecule, such as a recombinant protein derived from an antigen, an antibody or an enzyme, but also synthetic peptides and PNAs (peptide nucleic acids), to the surface of a support consisting of silica or metal oxides; it also relates to the supports thus prepared and to the uses which may be made of such a support.

2. Description of Related Art

Many methods exist for attaching biological molecules to silica supports. All of them involve a step of silanization of the silica which gives the surface the desired properties or functions. This functionalization then makes it possible to attach these compounds by adsorption, covalent coupling or complexation.

Firstly, there is the adsorption technique. Such a technique is, for example, described in patent applications EP-A-0, 368,208 and WO-A-91/02980. In this case, the proteins can adsorb onto a support via several paths of interaction (1). The main ones are hydrophobic, polar and ionic interactions. These interactions depend on both the support, the protein and the medium under consideration.

The hydrophobic adsorption is carried out by a method for adsorption onto a flat silica support employed in the laboratory (2), which uses the interactions between a silanized surface with long alkyl chains and one or more hydrophobic regions of the protein.

However, in terms of orientation of the elements on the alkyl chains, the attachment is not at all uniform, and only a small portion of the elements will be really available for subsequent reactions, which may limit sensitivity.

Secondly there is the coupling technique. In this respect, covalent bonding methods also exist, which use silica functionalized with silanes which terminate with functions of type: amine, thiol or epoxy. These functions react on the chemically reactive groups of the accessible amino acids of the protein. The covalent bonding then takes place directly or via coupling agents.

The covalent bonding of the protein to a support is irreversible and generally takes place on several accessible functions of a protein. As a result of this, there is sometimes an inhibition of the activity of the molecule.

For example, patent application EP-A-0,874,242 relates to the silanization of a support (silica oxide) to which biological molecules can be attached in completely random manner. The attachment is carried out in several steps; firstly, activation of the silanols, by hydrolysis of the oxygen bridges; secondly binding between the silanols and an intermediate attachment molecule which can accept a ligand.

There are thus at least two steps, which lengthens the duration of reaction and is not always compatible with good results, biological or otherwise, which makes attaching the ligand more complex, and which does not make it possible to orient the ligand. The attachment to the intermediate attachment molecule is then random.

Patent application EP-A-0,272,792 has notably the same drawbacks as the application described above, since it proposes to attach antigens to particles, still in a random manner. Here again, there is a second intermediate step which consists in providing cyanogen bromide, which, via covalent bonds, will indirectly associate the particles and antigens.

So, these two patent applications EP-A-0,874,242 and EP-A-0,272,792 are thus very far removed from one of the main objects of the present invention. This object consists in orienting the biological molecules attached to the support.

However, it is possible to selectively attach, in an oriented manner, a protein which has a "tag", for example lysine, as disclosed in the patent application FR 2 764 988, published Dec. 24, 1998.

All the same, there is no mention is this document of single-step attachment to a support consisting of silica or of metal oxide.

Thirdly, there is the chelation technique. In this way, a biological molecule can also be selectively attached to a support by chelation, according to a principle known to persons skilled in the art, such as the one employed for purifying proteins using the IMAC (Immobilized Metal ion-Affinity Chromatography) method on resins (3, 4). Such a protein possesses a histidine-rich labeling, termed "tag". The difficulty of the method consists in generating a support having divalent ions which are required for the chelation. Such an approach is disclosed in the patent application FR 2 762 394, published Oct. 23, 1998. According to this invention, a method for attaching biological material makes it possible to optimize the complexation of this material with a metal complex, while onto the same decreasing, or even eliminating, any side reaction of adsorption of said material onto the metal complex. For this purpose, the method for attaching a biological material, of the invention, uses a coordination ligand compound, or a complex compound obtained from the latter, said ligand compound being in microparticulate form or in linear form, and consisting of at least one particulate or linear polymer, with an exposed hydrophilic surface and covalently-bonded free complexing groups.

SUMMARY OF THE INVENTION

The subject of the present invention is to enable the attachment of a biological molecule, such as a recombinant protein derived from an antigen, an antibody or an enzyme, but also of synthetic peptides and of PNAs (peptide nucleic acids) to silica or metal oxide supports. This immobilization uses interactions between the silanols of the silica, or the alcohol functions of the metal oxides, and a region which is specific to the protein. The specific properties of the biospecific support thus created are mainly a good orientation of the biological molecules or ligands at the surface and a support engendering very good signal to background noise ratios. In addition, this type of immobilization is simple and stable over time.

To this effect, the present invention relates to a method for attaching a biological molecule to the surface of a support consisting of silica or of metal oxide, the molecule comprising a specific binding site, characterized in that it consists in:

functionalizing the surface of the support by cleaning, using at least one solvent or an oxygen plasma or any other process for forming alcohol groups on the surface of the support, in order to render said surface hydrophilic bringing the biological molecule directly into contact with said surface, and functionalizing said support by attaching the specific binding site of the biological molecule to at least one of the alcohol groups borne by the surface of the support, which allows the molecule to be oriented for better reactivity.

According to one preferential embodiment, the method comprises, before the bringing into contact, a step of immersion of the functionalized surface in a sulfochromic mixture.

In all instances, the specific binding site of the biological molecule comprises the following characteristics:

- it is an added amino acid sequence, i.e. added to the original sequence of the biological molecule,
- this sequence is introduced into a preferred site of the original sequence, where it is exposed in a way which is relevant with respect to its function or to its properties, and
- it contains in particular amino acids which are advantageous with respect to the desired function.

According to a first embodiment, the specific binding site of the biological molecule is a site rich in histidines and derivatives thereof, such as a site containing a sufficient density of histidines, in particular higher than or equal to 25%, and preferably higher than or equal to 33%.

More specifically, according to a second embodiment, the biological molecule and the specific binding site constitute a recombinant protein comprising at least two adjacent histidines called "tag".

In particular, according to a third embodiment, the specific binding site of the biological molecule comprises at least four histidines, and preferably six adjacent histidines.

Whatever the case, the specific site is located within the recombinant protein or preferably at its N-terminal or C-terminal end.

The bringing into contact is carried out for 30 to 60 minutes.

More specifically, the bringing into contact is carried out for 45 minutes.

The immersion step is carried out for 5 to 30 minutes.

More specifically, the immersion step is carried out for 15 minutes.

The method is carried out at an optimum hydrogen potential (pH) as a function of the physicochemical properties of the biological molecule and of the specific binding site, preferably between 6 and 7.5.

The present invention also relates to a surface of a support, functionalized by the method described above.

In a preferential embodiment, the surface is flat.

In another embodiment, the surface consists of a bead.

The present invention also relates to the use of a functionalized surface of a support, as described above, or manufactured by the method described above, characterized in that it consists in carrying out assays to detect, in a liquid to be analyzed, the presence of any biological molecule capable of attaching, via a specific binding site, to the support.

In a preferential embodiment, a functionalized surface of a support, as described above, or manufactured by the method described above, is used for carrying out immunological assays to detect, in a liquid to be analyzed, the presence of antibodies specific for a natural protein, for example the P24 protein, by specific binding, in the same way as with the natural protein, to at least one recombinant protein, for example the RH24 or R24 protein.

This P24 protein is a recombinant protein of the type 1 human immunodeficiency virus (HIV-1) capsid.

The attached figures are given by way of indicating examples, and have no limiting nature with regard to the exact scope of the present invention.

(A) very hydrophobic support, (B) relatively nonhydrophobic support and (C) very hydrophilic support.

Figure 2:
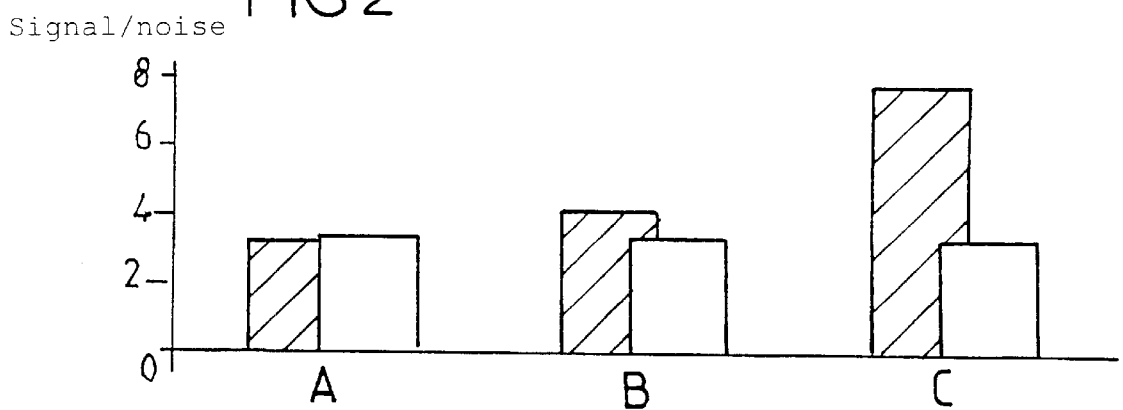

FIG. 2 represents a comparative graph of the signal/noise coefficient of the RH24 and R24 absorbed protein system on various supports.

Figure 3:
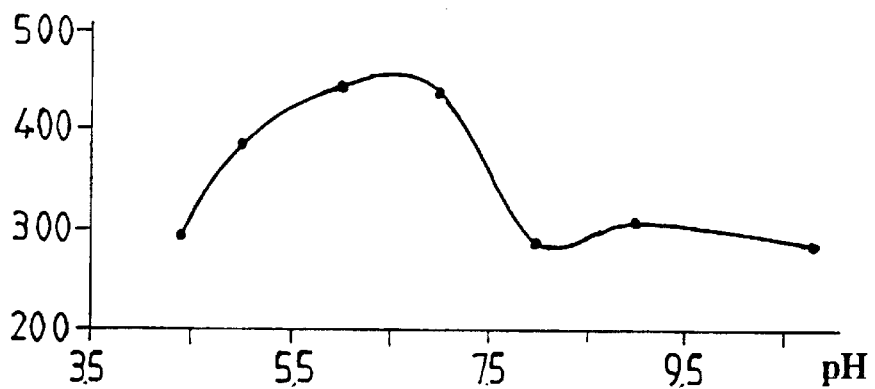

FIG. 3 represents a curve of effect of pH on the absorption of RH24 onto silica.

FIG. 4 represents a curve of assay of 15F8C7 monoclonal antibodies by SFMIA (Scanning Force Microscopic ImmunoAssay).

Finally, FIG. 5 represents a curve of assay of rabbit polyclonal antibodies by SFMIA; R24 (-●-) and RH24 (-▲-).

DETAILED DESCRIPTION OF PREFERRED EMBODIMENTS

A flat silicon oxide or silica support and a recombinant protein of the type 1 human immunodeficiency virus (HIV-1) capsid are used as a model. This system makes it possible to exploit atomic force microscopy (AFM) as a method for immunological analysis or SFMIA (2).

The protein under consideration herein is RH24. It is obtained using the conventional methods of molecular biology and of eukaryotic expression (5). This protein is practically similar to RH24 (identical immunogenicity), but is much more easily purified due to the presence of a small sequence of additional amino acids. This series of amino acids, named "tag", contains in particular six consecutive histidines. The affinity of such a molecular motif for certain metal ions is extremely high. This property enables easy purification using the IMAC (immbolized metal ion-affinity chromatography) technique. The control protein without the "tag" is R24. It is obtained in the same way as RH24, but it is purified by immunoaffinity.

The specific binding sites can be in the form of continuations of said amino acids, which may be identical or different, contiguous or noncontiguous, but are close.

The definition of the "tag" is as follows:

1/ it is an added sequence of amino acids, i.e. added to the original sequence (protein, peptide, PNA), 2/ this sequence is introduced into a preferred site of the original sequence, where it is exposed in a way which is relevant with respect to its function (or to its properties, for example chelation, coupling, interactions with a specific support, etc.), in particular the N-terminal and C-terminal ends of the recombinant proteins or of the synthetic peptides or of the PNAs, and 3/ it contains in particular amino acids which are advantageous with respect to the desired function, in our case histidines, distributed within the sequence, either contiguously (in particular two contiguous histidines, preferably six contiguous histidines), or with a sufficient density (in particular 25%, preferably higher than or equal to 33%).

Advantageously, said binding site comprises from three to ten amino acids, contiguous or noncontiguous, for an ordered primary structure of the protein material comprising at least thirty amino acids. As a preferred variant, it consists of at least two, preferably at least three, and preferentially at least six histidine residues, and more particularly, these residues are contiguous.

The site(s) described above can be found at any place in the primary structure of the protein material. Preferably, it is located on the N-terminal or C-terminal end of the protein material.

Silica, which is available in many forms (flat surfaces, beads, fibers, etc.), is a compound widely used in microelectronics. However, research into medical diagnostics is focusing more and more on so-called "integrated" systems (DNA chips, biochips, etc.) comprising chips which are sensitive to biological molecules. Such technology would ally sensitivity, rapidity and miniaturization.

In addition it is possible to obtain silica surfaces with a roughness which does not exceed a few Angstroms. This property then allows the use of an extremely powerful means of detection and analysis: atomic force microscopy (AFM). Atomic force microscopy provides both the observation of surfaces functionalized with biological molecules, and very sensitive immunoassays (2).

It appeared that RH24 has a natural affinity for silica supports. This property originates from a strong direct interaction between the surface of a support and the poly(histidine) sequence.

The present invention is thus directed toward attaching a recombinant protein to silica via its histidine sequence. This technique also makes it possible to orient such a protein on the surface. Specifically, if the exposed region of the molecule is a recognition site, then it is all the more reactive (enzyme active site or immunodominant epitope, for example).

More specifically, the invention relates to the oriented attachment of RH24, and of any recombinant protein, to silica. It is thus along these lines. Complete information on the R24 protein and its recombinants RH24 and RH24K can be found in a previous patent application by the applicant, filed on Jun. 20, 1997 under the number FR 97/08055. The content of this application is incorporated in the present invention.

The invention relates to a direct attachment process, without silanization of the silica, for binding between the silica and the recombinant protein.

The approach uses the specific affinity of the RH24 "tag" for hydrophilic silica. This attachment technique is novel and extremely simple and robust. It is the subject of the protection sought by the present invention.

The advantage of this immobilization according to the second approach is to be found in two major techniques; on the one hand, ELISA for its simplicity and its robustness, and on the other hand, immunological assay by AFM (SFMIA) for its finesse and its sensitivity.

EXAMPLE 1

Manufacturing the Biospecific Support

By way of comparison, the adsorption of R24 and of RH24 onto various silica supports was tested. Three types of flat silica support were used:

a naked silica which is partially hydrophobic since it is not cleaned and not hydrolyzed with the sulfochromic mixture, a silica which is very hydrophilic since it is cleaned and hydrolyzed with the sulfochromic mixture, and a very hydrophobic silica functionalized with n-octadecyldimethylmethoxysilane.

The supports used herein are silicon wafers (4" polished wafers from ACM (France), P-doped N-type, 525 micrometers ($\mu$m) thick, orientation <100>).

Initially, the wafers are cleaved into square blocks of 0.64 cm$^2$.

1) Partially Hydrophobic Naked Silica:

The cleaved blocks have at their surface a layer of silicon oxide, which is native or obtained by the various methods known to persons skilled in the art. This oxide layer has, inter alia, hydrophobic siloxane bridges, and it may be polluted with atmospheric contaminants.

A silica of this type is partially hydrophobic.

2) Very Hydrophilic Silica:

In order to obtain hydrophilic silica supports which are clean and have the desired size, the blocks undergo the following treatment:

surface cleaning: the silicon blocks are washed with diverse solvents; used, in this order, are: water, ethanol, acetone, dichloromethane and toluene, and hydrolyzing the siloxane bridges to silanols: the silica supports are immersed for 15 minutes in a sulfochromic mixture (PROLABO solution saturated with chromium (VI) oxide in 95% sulfuric acid). The surfaces are thoroughly rinsed with water and transferred to an ultrasound bath; once the blocks have been dried with nitrogen, they are quickly used in order to limit rapid recontamination.

The main property of a clean silica is its great hydrophilicity. This can be verified by measuring the angle of contact (angle between the tangent along the edge of the drop of water and the surface of the support), which should be less than or equal to 10°.

3) Hydrophobic Silica:

The blocks are cleaned as described above (paragraph 2).

Then, the silica is made hydrophobic by bringing n-octadecyldimethylmethoxysilane, which is a silane bearing a long alkyl chain, at 2% in toluene, into contact for three hours at room temperature. The blocks are then washed thoroughly with water, cleaned by ultrasound and stabilized for two hours at 120° C.

4) Adsorption of Proteins onto the Various Supports Described:

In the case of R24 or of RH24, it is possible to carry out adsorption onto a hydrophilic support (support described in paragraph 2) or a hydrophobic support (supports described in paragraphs 1 and 3).

In the case of adsorption onto a hydrophilic support, there is no need to functionalize the previously treated silica surface; it is considered to be already functionalized.

This technique is conventionally never used on hydrophilic naked silica. Specifically, these interactions are generally too fragile (very sensitive to pH and to variations in ionic strength). However, in the case of RH24, or of any other "ligands" as defined above, the presence of the "tag" makes this adsorption extremely advantageous, since it is very easy to carry out.

*40 microliters of RH24 (or of R24 as control) diluted in PBS are incubated for 45 minutes at room temperature on hydrophilic silica.

RH24 has a strong affinity for silica. The advantage of this affinity is its specificity toward RH24 in comparison with R24. From this point onward, the analysis which follows attempts to understand more clearly the role of the "tag".

*40 microliters of protein solution in PBS are incubated for 2 hours at room temperature on the silanized blocks. Then, they are rinsed with PBS-Tween (0.05% Tween in PBS).

EXAMPLE 2

Biospecific Support Tests

The presence and orientation of R24 and of RH24 are revealed with two types of immunoassay: ELISA and SFMIA.

The presence of R24 or of RH24 at the surface of the support is evaluated by means of antibodies. Polyclonal or monoclonal solutions are used. A 40 $\mu$l drop of antibodies in solution in the PBS-TWEEN-BSA [0.05% of BSA (w/w) in PBS-TWEEN] mixture at the desired concentration is placed on a block for 1 hour at 37° C. The BSA makes it possible, as does the TWEEN, to limit nonspecific interactions. The silicon square is then washed with PBS-TWEEN-BSA in order to remove a maximum amount of the antibodies which have adsorbed onto the support but not attached to the protein. The blocks are dried with compressed air.

1) Enzymatic Assay (ELISA):

The amount of biotinylated antibodies captured by the recombinant protein is evaluated with an enzymatic assay. An alkaline phosphatase (ALP)-Streptavidin complex is attached first of all. For this, 40 µl of a solution of 4 g/ml of Streptavidin-ALP in PBS-TWEEN-BSA are reacted at 37° C. for 45 minutes.

Then, the presence of the enzyme is revealed by adding a colorimetric substrate, p-nitophenyl phosphate (pnPP). A block is immersed in 0.8 ml of pnPP solution at 2 mg/ml in its buffer. The enzyme is left to react with its substrate for 45 minutes at 37° C. Then, the reaction is stopped by adding 0.8 ml of 1N sodium hydroxide.

The calorimetric assay at 405 nm is performed on 100 µl of solution in AXIA reader microplates. The OD obtained is related to the concentration of protein at the surface.

2) SFMIA Assay:

The amount of biotinylated antibodies, captured by the recombinant protein, on the support is evaluated by means of an AFM topographic label:

*40 µl of a 5% (V/V) solution of magnetic beads, 50 nm in diameter, covered with Streptavidin are deposited on the support for 1 hour. In order to help the surface reaction, the supports are placed on powerful magnets made of rare earth metals. Then, the blocks are rinsed with water and dried with compressed air.

The number of magnetic beads at the surface is proportional to the amount of proteins retained on the support. This number of beads is quantified by AFM.

EXAMPLE 3

Comparison of the Methods of Attachment of R24 and RH24

Figure 1:
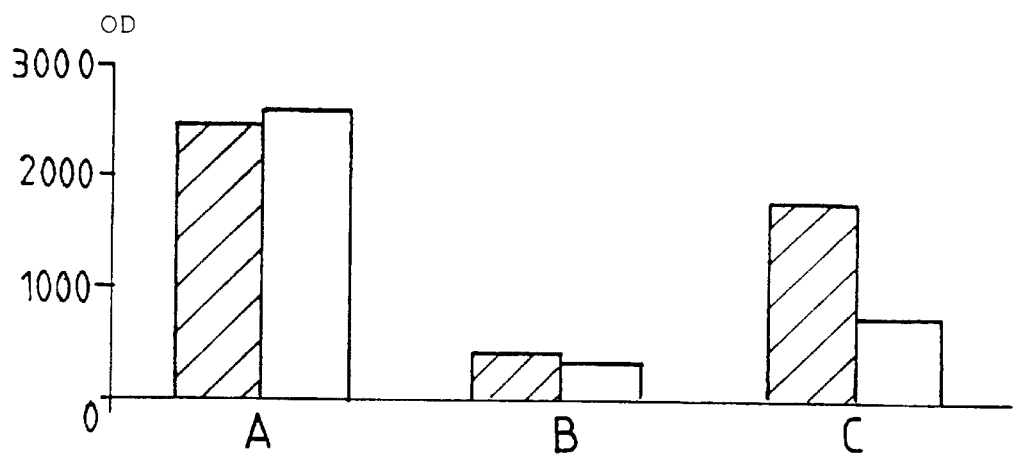
FIG. 1 represents a comparative graph of the optical density (OD) obtained in an ELISA assay of RH24 (▨) and R24 (☐) absorbed onto various supports.

The results in FIG. 1 are obtained for protein concentrations of 10 µg/ml revealed by ELISA with the antibody 13B5 at 1 µg/ml under standard conditions.

This antibody was the subject of the filing of a French patent application, by the applicant, on the same day as this patent application. The title of this other application is: "Ligand peptidique présentant une affinité spécifique vis à vis de la protéine P24 du rétrovirus HIV" [Peptide ligand having specific affinity with respect to the P24 protein of the HIV retrovirus].

Only the hydrophilic silica support shows a significant difference in signal between R24 and RH24. This shows that the RH24 "tag" plays a specific role in the hydrophilic adsorption.

On the other hand, if the graph of the signal/noise ratios is plotted, the results obtained are given in FIG. 2.

Besides the specificity of adsorption onto a hydrophilic support, this support makes it possible to obtain an excellent signal/noise coefficient. This probably originates from the fact that there is little adsorption of antibodies onto a hydrophilic support (the Fc of antibodies is rather hydrophobic).

Limiting the background noise is an essential factor for producing sensitive detection systems. So, even if the crude signal obtained is slightly lower than that of a hydrophobic surface, the gain in background noise makes it a potentially more advantageous system.

1) pH and Ionic Strength:

The affinity of RH24 for silica is notable since it is relatively insensitive to the ionic strength of the surrounding medium. Thus, rinsing in water or with a solution of 9 M NaI have no effect on the surface. RH24, once attached, is thus strongly bound to the support.

RH24 was diluted to 1 µg/ml in various phosphate buffers, the pHs of which vary between 4 and 11. Then, it is adsorbed and revealed with a standard ELISA assay using rabbit polyclonal at 1 µg/ml. The optimum adsorption conditions obtained are located between 6 and 7 (see FIG. 3).

Since it is known that the isoelectric point of the protein is 6.05, that the pKa of a polyhistidine sequence is 6, and that the pKa of silanols is between 4 an 7, this result is coherent with several possible methods of interaction (bonds induced between the aromatic ring of the histidine and the silanols, hydrogen bonds between the silanols and the electron donor or acceptor groups, electrostatic bonds between deprotonized silanols ($-SiO^-$) and imidazole nuclei positively charged at pH lower than or equal to 6. Since the "tag" has a local overconcentration of these various types of interaction, this makes it possible to explain the affinity and the solidity of the binding.

2) Binding Strength:

In order to demonstrate that the "tag" has effectively a great affinity for the support, RH24 was adsorbed in competition with a polypeptide having a sequence equivalent to the "tag" (MRGSHHHHHHSVDES). For this, a solution of $3.7 \times 10^{-7}$ [sic] mol/l of RH24 (10 µg/ml) and of $3.7 \times 10^{-4}$ [sic] mol/l of polypeptide is prepared (1 molecule of RH24 per 1000 molecules of polypeptide). Then, the block is incubated with this mixture, and revealed by ELISA with the monoclonal 13B5D10 at 1 µg/ml. The following results are obtained:

TABLE III

Density obtained for a "tag"/RH24 mixture

| Reaction | Optical density (background noise subtracted) |
| --- | --- |
| Polypeptide/RH24 mixture | 110 |
| Protein alone | 780 |

The signal decreases by more than 85% in the presence of the polypeptide, which suggests that the sequence, by occupying the attachment sites, prevents RH24 from attaching to its support.

This result was also obtained by competition with pyridine, but a 0.11 mol/l solution was necessary to reduce the signal by more than 70% (1 molecule of RH24 per 300 000 molecules of pyridine). Since it is known that the affinity of pyridine for the surface of silica is considered to be very high, it is clear that the RH24 "tag" has an excellent affinity for the support. Such results could not be obtained with imidazole. This shows that the strong interaction between RH24 and the surface originates not only from the nature of the groups concerned, but also from their number in the "tag". This multiple bond cooperative effect explains the strength of this binding.

All these results make it possible to conclude that the affinity of RH24 for silica is high. The model of multiple bonds between the "tag" and the silanols was demonstrated indirectly by competition.

3) Orientation:

The sensitivity of the system for detecting RH24 on a silica support is evaluated by means of an SFMIA.

A 10 µg/ml protein solution is incubated on blocks. These blocks are revealed by SFMIA using polyclonal and monoclonal antibodies (15F8C7) labeled with magnetic particles. The amount of magnetic beads covering the surface is evaluated using the image-processing system. The curves of percentage of covering as a function of the concentration of antibodies used are thus plotted in FIGS. 4 and 5.

The results obtained by SFMIA show a considerable difference in signal between R24 and RH24 when a monoclonal antibody is used.

Since the monoclonals used are not directed against the "tag", they have intrinsically the same reactivity with respect to R24 and RH24. The increase in signal concerning RH24 may originate from two phenomena. RH24 is more concentrated on the surface than R24, or RH24 is oriented on its support.

If RH24 is partially oriented on its support, then the epitope for attachment of the monoclonal antibody is more frequently accessible.

In fact, in the case of ORIENTATED ATTACHMENT, the epitope recognized by the monoclonal is ALWAYS or NEVER accessible, whereas in the case of a RANDOM ATTACHMENT, it will be accessible only SOMETIMES. The result of this is thus an increase in the signal by immunoassay on this monoclonal. This amplification of the signal will not occur with a polyclonal on RH24, because this polyclonal has no immunodominant epitope. Orienting such a protein on a support thus has no value for a polyclonal solution.

If the effect is due to the surface concentration, this must originate from a specific interaction engendered by the "tag". Since this interaction is geographically located on the protein, it cannot, therefore, be dissociated from an effect of orientation.

4) Conclusions:

The experiments carried out clearly show that the specificity of the interaction between the silica and RH24 originates from the specific binding site or "tag".

The immobilization obtained is relatively insensitive to variations in ionic strength, and conserves its immunogenic properties over a long period. In addition, this support gives much better signal/noise ratios than a system by adsorption onto a hydrophobic support.

Standard assays for enzymatic assaying of anti-R24 antibodies are conventionally carried out on supports (polystyrene wells) onto which the protein is adsorbed by hydrophobic interactions. The detection limits obtained by adsorption onto hydrophilic silica are comparable to these immunoassays.

In addition, the flat support used is suitable for the use of atomic force microscopy. The SFMIA assays carried out with magnetic beads, as described in patent application FR 2 758 884, published Jul. 31, 1998, make it possible to perform high sensitivity immunoassays.

The systematic comparison between RH24 and R24, in the case of the immunoassays showed a similarity in behavior with respect to a polyclonal, and a notable difference with respect to the monoclonal antibodies. The orientation of RH24 at the surface is the best explanation thereof.

BIBLIOGRAPHY (1) Gautier, S., Aimé, J. P., Bouhacina, T., Attias, A. J., Desbat, B., *Langmuir* 12, 5126 (1996).

(2) Perrin, A., Lanet, V., Theretz, A., *Langmuir* 13, 2557 (1997).

(3) Porath J., Carlsson., Olsson., Belfrage J., *Nature*, 258, 598 (1975).

(4) Porath J., *Trends Anal. Chem.*, 7, 254 (1988).

(5) Cheynet, V., Verrier, B., Mallet, F., *Protéine Expr. Purif. L,* 367–372 (1993).

What is claimed is:

1. A method for detecting and/or measuring the amount of a target anti-ligand in a liquid, comprising the following steps:

(a) starting from first ligand comprising a first sequence of amino acids having a specific recognition site for said anti-ligand;

(b) deriving a ligand from said first ligand, said derived ligand comprising a sequence of amino acids derived from said first sequence, said derived sequence differing from said first sequence at least in that said derived sequence comprises at least one added tag histidine site comprising at least two histidines or histidine derivatives, said tag site being different from said recognition site;

(c) starting from a support comprising at least one of silica and a metal oxide, said support having an exposed surface;

(d) functionalizing the exposed surface so as to form alcohol groups said surface, rendering said surface hydrophilic;

(e) contacting the functionalized exposed surface of the support with the derived ligand, so as to directly interact and attach by adsorption said tag histidine site of said derived ligand with said alcohol groups of said exposed functionalized surface, to obtain an affinity support with oriented recognition sites;

(f) contacting said affinity support with said liquid; and (g) detecting and/or measuring the anti-ligand bound to said affinity support.

2. A method according to claim 1, wherein step (d) is carried out by at least one technique selected from the group consisting a cleaning, using at least one solvent, and using a plasma.

3. A method according to claim 1, wherein, before step (e), the exposed functionalized surface is immersed in a sulfochromic mixture.

4. A method according to claim 1, wherein said tag histidine site of said derived ligand comprises a sequence having at least two contiguous histidines or histidine derivatives.

5. A method according to claim 1, wherein said tag histidine site of said derived ligand comprises at least four contiguous histidines or histidine derivatives.

6. A method according to claim 1, wherein said tag histidine site of said derived ligand comprises at least six contiguous histidines or histidine derivatives.

7. A method according to claim 1, wherein said tag histidine site is located at the N-terminal end of said derived ligand.

8. A method according to claim 1, wherein said tag histidine site is located at the C-terminal end of said derived ligand.

9. A method according to claim 1, wherein said tag histidine site has from three to ten histidine or histidine residues.

10. A method according to claim 1, wherein the recognition site is selected in the group consisting of enzyme active sites and immunodominant epitopes.

11. A method according to claim 1, wherein step (f) is carried out by a technique selected from the group consisting of enzymatic assays, immuno-assays, scanning force microscopic immuno-assays, and atomic force microscopy.

12. A method according to claim 1, wherein the firs ligand is a natural protein selected in the group consisting of antigens, antibodies, enzymes, synthetic peptides, and peptide nucleic acids, and the derived ligand is a recombinant protein.

13. A method according to claim 12, wherein the natural protein is the P24 protein of the type 1 human immunodeficiency virus (HIV1) capsid, and the derived ligand is the RH24 protein.

* * * * *